US011883565B2

(12) United States Patent
Tang et al.

(10) Patent No.: US 11,883,565 B2
(45) Date of Patent: Jan. 30, 2024

(54) URETERAL STENT

(71) Applicant: Gyrus ACMI, Inc., Southborough, MA (US)

(72) Inventors: Hui Tang, Acton, MA (US); Thomas J. Holman, Princeton, MN (US); Judy L Walish, West Roxbury, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 445 days.

(21) Appl. No.: 15/921,100

(22) Filed: Mar. 14, 2018

(65) Prior Publication Data

US 2018/0272041 A1 Sep. 27, 2018

Related U.S. Application Data

(60) Provisional application No. 62/472,707, filed on Mar. 17, 2017.

(51) Int. Cl.
| | |
|---|---|
| A61L 31/04 | (2006.01) |
| A61F 2/04 | (2013.01) |
| A61L 31/02 | (2006.01) |
| A61L 31/12 | (2006.01) |
| A61M 27/00 | (2006.01) |

(52) U.S. Cl.
CPC ............ *A61L 31/041* (2013.01); *A61F 2/04* (2013.01); *A61L 31/028* (2013.01); *A61L 31/128* (2013.01); *A61L 31/129* (2013.01); *A61F 2002/048* (2013.01); *A61F 2240/001* (2013.01); *A61F 2250/0018* (2013.01); *A61M 27/008* (2013.01); *A61M 2205/0216* (2013.01); *A61M 2207/00* (2013.01)

(58) Field of Classification Search
CPC .... A61L 31/041; A61L 31/129; A61L 31/028; A61L 31/128; A61L 31/16; A61L 31/148; A61F 2/04; A61F 2250/0018; A61F 2002/048; A61F 2240/001; A61F 2250/0067; A61F 2210/0004; A61F 2220/0008; A61M 27/008; A61M 2207/00; A61M 2205/0216; A61K 31/00; A61K 9/0036

See application file for complete search history.

(56) References Cited

U.S. PATENT DOCUMENTS

| | | | |
|---|---|---|---|
| 9,034,346 B2 | 5/2015 | Miller et al. | |
| 9,445,884 B2 | 9/2016 | Barron et al. | |
| 2003/0153983 A1* | 8/2003 | Miller ..................... | A61L 2/232 623/23.71 |
| 2003/0224033 A1* | 12/2003 | Li ........................ | A61K 9/0024 604/529 |
| 2004/0236416 A1* | 11/2004 | Falotico .................. | A61L 31/10 623/1.42 |
| 2004/0243216 A1* | 12/2004 | Gregorich ............... | A61F 2/915 623/1.15 |
| 2004/0267362 A1* | 12/2004 | Hwang ............... | A61L 27/3645 623/13.17 |
| 2005/0096733 A1* | 5/2005 | Kovneristy ............... | A61F 2/90 623/1.22 |
| 2005/0113806 A1* | 5/2005 | De Carvalho ............ | A61F 2/02 604/890.1 |
| 2006/0259051 A1* | 11/2006 | Nissl ......................... | A61F 2/04 606/153 |
| 2007/0020381 A1* | 1/2007 | Hossainy ................ | A61L 31/16 623/1.42 |
| 2007/0150051 A1* | 6/2007 | Arnault De La Menardiere ........ | A61F 2/90 600/36 |
| 2008/0075779 A1* | 3/2008 | Chappa .................. | A61L 31/16 514/772.3 |
| 2008/0255657 A1* | 10/2008 | Gregorich ................. | A61F 2/86 623/1.42 |
| 2012/0010691 A1* | 1/2012 | Clarke ...................... | A61F 2/91 623/1.42 |
| 2017/0027682 A1* | 2/2017 | Merk ........................ | A61F 2/07 |

OTHER PUBLICATIONS

A. N. Gent "On the Relation between Indentation Hardness and Young's Modulus", Sep. 1, 1958, Rubber Chemistry and Technology, 31 (4): Abstract (Year: 1958).*

Liu et al., "Evaluation of two polymeric blends (EVA/PLA and EVA/PEG) as coating film materials for paclitaxel-eluting stent application", Jan. 8, 2011, J Mater Sci: Mater Med, 22, pp. 327-337 (Year: 2011).*

Baer et al., "Thermomechanical Properties, Collapse Pressure, and Expansion of Shape Memory Polymer Neurovascular Stent Prototypes", Jul. 2009, J Biomed Mater Res B Appl Biomater, 90(1), pp. 421-429 (Year: 2009).*

Tambaca et al., "Mechanical Behavior of Fully Expanded Commercially Available Endovascular", 2011, Tex Heart Inst J, 38(5), pp. 491-501 (Year: 2011).*

* cited by examiner

*Primary Examiner* — Guy K Townsend
*Assistant Examiner* — Alessandro R Del Priore
(74) *Attorney, Agent, or Firm* — Schwegman Lundberg & Woessner, P.A.

(57) ABSTRACT

Provided is a ureteral stent comprising certain amount of ethylene-vinyl acetate polymer and a certain amount of an additive selected from barium sulfate, bismuth subcarbonate, bismuth oxychloride, a polyolefin elastomer, a thermoplastics elastomer, and a mixture thereof. The provided stent may have multiple layers such as inner layer and outer layer with each layer having different elastic modulus. Also provided is a method of making the aforementioned ureteral stent and a method of using the ureteral stent in treating kidney or bladder related diseases.

16 Claims, 12 Drawing Sheets

URETERAL STENT

CROSS-REFERENCE TO RELATED PATENTS

This application claims the benefit of priority to U.S. Provisional Patent Application No. 62/472,707 filed on Mar. 17, 2017. The entire teachings of the above application are incorporated herein by reference.

TECHNICAL FIELD

The embodiments of the present disclosure relate generally to medical devices. More particularly, the embodiments of this disclosure relate to stents made from poly ethylene vinyl acetate polymer and other thermoplastic elastomers. Even more particularly, the embodiments of this disclosure relate to ureteral stents made from certain amount of poly ethylene vinyl acetate polymer and certain amount of other thermoplastic elastomers.

BACKGROUND

U.S. Pat. No. 9,445,884 discloses ureteral stents that comprise an elongated stent body, at least one deployable retention structure, and at least one sleeve and/or sheet of drug-releasing material. In various disclosed embodiments, the at least one sleeve and/or sheet of drug-releasing material is deployed concurrently with the deployment of at least one deployable retention structure. The ureteral stents of the '884 patent are adapted to release the urologically beneficial drug into a subject.

U.S. Pat. No. 9,034,346 discloses implantable or insertable medical devices that provide resistance to microbial growth on and in the environment of the device and resistance to microbial adhesion and biofilm formation on the device. In particular, the '346 patent discloses implantable or insertable medical devices that comprise at least one biocompatible matrix polymer region, an antimicrobial agent for providing resistance to microbial growth and a microbial adhesion/biofilm synthesis inhibitor for inhibiting the attachment of microbes and the synthesis and accumulation of biofilm on the surface of the medical device. Also disclosed are methods of manufacturing such devices under conditions that substantially prevent preferential partitioning of any of said bioactive agents to a surface of the biocompatible matrix polymer and substantially prevent chemical modification of said bioactive agents.

SUMMARY OF THE DISCLOSURE

In one embodiment, the present disclosure provides a stent comprising ethylene-vinyl acetate in an amount of about 9% to about 40% by weight, and an additive selected from barium sulfate, bismuth subcarbonate, bismuth oxychloride, a polyolefin elastomer, a thermoplastics elastomer, and a mixture thereof in an amount of about 10% to about 90% by weight. In one embodiment, the stent has a density of lower than about 1.0 g/cm$^3$. In one embodiment, the stent has a density of between about 0.933 to about 0.952 g/cm$^3$. In one embodiment, the stent has a Vicat Softening temperature of about 39 to about 82° C. In one embodiment, the stent has a tensile stress of about 11 to about 26 MPa. In one embodiment, the stent has an elastic modulus of about 15 to about 123 MPa.

In one embodiment, the present disclosure provides a ureteral stent comprising ethylene-vinyl acetate in an amount of about 9% to about 40% by weight, and an additive selected from barium sulfate, bismuth subcarbonate, bismuth oxychloride, a polyolefin elastomer, a thermoplastics elastomer, and a mixture thereof in an amount of about 10% to about 90% by weight. In one embodiment, the ureteral stent has a density of lower than about 1.0 g/cm$^3$. In one embodiment, the ureteral stent has a density of between about 0.933 to about 0.952 g/cm$^3$. In one embodiment, the ureteral stent has a Vicat Softening temperature of about 39 to about 82° C. In one embodiment, the ureteral stent has a tensile stress of about 11 to about 26 MPa. In one embodiment, the ureteral stent has an elastic modulus of about 15 to about 123 MPa.

In one embodiment, the present disclosure also provides a method of making a comfort stent through multilayer tubing co-extrusion in combination with advanced microextrusion technologies. More particularly, the ureteral stents are made through the melt process of polymer compounding, and the functional additives may also be added to enhance or modify the properties of the ureteral stents.

In one embodiment, the present disclosure further provides a method of treating a kidney or a bladder related condition in a subject, the method comprising placing a comfort stent into a site of a subject that needs treatment through the known procedures. The treatment method may be in combination with other treatment methods or therapeutic agents.

DETAILED DESCRIPTION OF THE DISCLOSURE

Definitions

Figure 1:
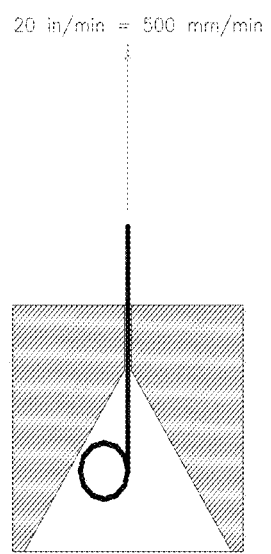
FIG. 1 shows funnel block for retention strength test.

Unless otherwise specified, the following terms and phrases shall have the meanings as set forth below:

The terms "one embodiment", "another embodiment", "some embodiments", "other embodiments", and similar expressions indicate that the embodiment or embodiments described may include a particular feature, structure, or characteristic, but every embodiment may not necessarily include the particular feature, structure, or characteristic. Moreover, such phrases are not necessarily referring to the same embodiment. Furthermore, when a particular feature, structure, or characteristic is described in connection with an embodiment, it would be within the knowledge of one skilled in the art to incorporate such feature, structure, or characteristic into other embodiments, whether or not explicitly described, unless clearly stated to the contrary. That is, the various individual elements described below, even if not explicitly shown in a particular combination, are nevertheless contemplated as being combinable with each other to form other additional embodiments or to complement and/or enrich the described embodiment or embodiments, as would be understood by one of ordinary skill in the art.

The articles "a", "an" and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to". The term "or" is used herein to mean, and is used interchangeably with, the term "and/or", unless context clearly indicates otherwise.

The term "such as" is used herein to mean, and is used interchangeably, with the phrase "such as but not limited to". Unless specifically stated or obvious from context, as used herein, the term "about" is understood as within a range of normal acceptance in the art, for example within standard deviations of the mean.

All numeric values are herein assumed to be modified by the term "about" whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. Even more specifically, "about" can be understood as within 10%, 9%, 8%, 7%, 6%, 5%, 4%, 3%, 2%, 1%, 0.5%, 0.1%, 0.05%, or 0.01% of the stated value.

Ranges provided herein are understood to be shorthand for all of the values within the range. For example, a range of 1 to 10 is understood to include any number, combination of numbers, or sub-ranges such as 1, 1.5, 2.0, 2.8, 3.90, 4, 5, 6, 7, 8, 9, and 10.

A percent by weight of a component of a composition refers to a percent of a component relative to the whole weight of the composition. For example, ethylene-vinyl acetate in an amount of about 10% by weight refers to a composition comprising about 10% by weight ethylene-vinyl acetate relative to the whole weight of the composition. Or put it another way, the composition has a content of about 10% by weight of ethylene-vinyl acetate, and other components make up the remaining about 90% of the composition.

As used herein, the term "subject" refers to human and non-human animals, including veterinary subjects. The term "non-human animal" includes all vertebrates, e.g., mammals and non-mammals, such as non-human primates, mice, rabbits, sheep, dog, cat, horse, cow, chickens, amphibians, and reptiles. In a preferred embodiment, the subject is a human and may be referred to as a patient.

As used herein, the terms "treat", "treating" or "treatment" refers, preferably, to an action to obtain a beneficial or desired clinical result including, but not limited to, alleviation or amelioration of one or more signs or symptoms of a disease or condition, diminishing the extent of disease, stability (i.e., not worsening) state of disease, amelioration or palliation of the disease state, diminishing rate of or time to progression, and remission (whether partial or total), whether detectable or undetectable. "Treatment" can also mean prolonging survival as compared to expected survival in the absence of treatment. Treatment does not need to be curative.

As used herein, the terms "therapeutic agent" and "therapeutic agents" refer to any agent(s) which can be used in the treatment, management, or amelioration of a disease or a condition or one or more symptoms thereof. Preferably, a therapeutic agent is an agent that is known to be useful for, or has been or is currently being used for the treatment, management, prevention, or amelioration of a disease or a condition or one or more symptoms thereof.

As used herein, the term "Vicat softening temperature" or "Vicat hardness" is the determination of the softening point for materials that have no definite melting point, such as plastics. It is taken as the temperature at which the specimen is penetrated to a depth of 1 mm by a flat-ended needle with a 1 $mm^2$ circular or square cross-section. For the Vicat A test, a load of 10 N is used. For the Vicat B test, the load is 50 N.

Standards to determine Vicat softening point include ASTMD 1525 and ISO 306, which are largely equivalent. The Vicat softening temperature can be used to compare the heat-characteristics of different materials. Four different methods may be used for testing: method A50 with load (N) 10 at heating rate (K/h) of 50; method B50 with load (N) 50 at heating rate (K/h) of 50; method A120 with load (N) 10 at heating rate (K/h) of 120; and method B120 with load (N) 50 at heating rate (K/h) of 120.

As used herein, the term "ultimate tensile strength (UTS)", often shortened to "tensile strength" (TS) or "ultimate strength", is the capacity of a material or structure to withstand loads tending to elongate, as opposed to compressive strength, which withstands loads tending to reduce size. In other words, tensile strength resists tension (being pulled apart), whereas compressive strength resists compression (being pushed together). Ultimate tensile strength is measured by the maximum stress that a material can withstand while being stretched or pulled before breaking. In the study of strength of materials, tensile strength, compressive strength, and shear strength can be analyzed independently.

The UTS is usually found by performing a tensile test and recording the engineering stress versus strain. The highest point of the stress-strain curve is the UTS. It is an intensive property; therefore, its value does not depend on the size of the test specimen. However, it is dependent on other factors, such as the preparation of the specimen, the presence or otherwise of surface defects, and the temperature of the test environment and material.

Tensile strength is defined as a stress, which is measured as force per unit area. For some non-homogeneous materials (or for assembled components) it can be reported just as a force or as a force per unit width. In the International System of Units (SI), the unit is the pascal (Pa) (or a multiple thereof, often megapascals (MPa), using the SI prefix mega); or, equivalently to pascals, newtons per square metre ($N/m^2$). A United States customary unit is pounds per square inch (lb/int or psi), or kilo-pounds per square inch (ksi, or sometimes kpsi), which is equal to 1000 psi; kilo-pounds per square inch are commonly used in one country (US), when measuring tensile strengths.

As used herein, the term "flexural modulus" or "bending modulus" is an intensive property that is computed as the ratio of stress to strain in elastic deformation, or the tendency for a material to bend. It is determined from the slope of a stress-strain curve produced by a flexural test (such as the ASTM D790), and uses units of force per area. Ideally, elastic or bending modulus of elasticity is equivalent to the tensile or compressive modulus of elasticity. In reality, these values may be different, especially for plastic materials.

As used herein, the term "polyolefin elastomers" (POE) are copolymers of ethylene and another alpha-olefin such as butene or octene. The metallocene catalyst selectively polymerizes the ethylene and comonomer sequences and increasing the comonomer content will produce polymers with higher elasticity as the comonomer incorporation disrupts the polyethylene crystallinity. Furthermore, the molecular weight of the copolymer will help determine its processing characteristics and end-use performance properties with higher molecular weights providing enhanced polymer toughness.

POEs are produced using refined metallocene catalyst (often referred to as single-site or constrained geometry catalyst). These catalysts have a constrained transition metal (generally a Group 4B metal such as Ti, Zr, or Hf) sandwiched between one or more cyclopentadienyl ring structures to form a sterically hindered polymerization site. This unique catalyst provides a single polymerization site instead of the multiple sites of conventional catalysts and provides the capability to tailor the molecular architecture of ethylene copolymers.

As used herein, the term "thermoplastic elastomers" (TPE), sometimes referred to as thermoplastic rubbers, are a class of copolymers or a physical mix of polymers (usually a plastic and a rubber) which consist of materials with both thermoplastic and elastomeric properties. While most elastomers are thermosets, thermoplastics are in contrast relatively easy to use in manufacturing, for example, by injection molding. Thermoplastic elastomers show advantages typical of both rubbery materials and plastic materials. The benefit of using thermoplastic elastomers is the ability to stretch to moderate elongations and return to its near original shape creating a longer life and better physical range than other materials. The principal difference between thermoset elastomers and thermoplastic elastomers is the type of cross-linking bond in their structures. In fact, crosslinking is a critical structural factor which imparts high elastic properties.

Reference will now be made in detail to preferred embodiments of the present disclosure. While the disclosure will be described in conjunction with the preferred embodiments, it will be understood that it is not intended to limit the disclosure to those preferred embodiments. To the contrary, it is intended to cover alternatives, modifications, and equivalents as may be included within the spirit and scope of the disclosure as defined by the appended claims.

In one embodiment, the present disclosure provides a stent comprising ethylene-vinyl acetate in an amount of about 9% to about 40% by weight, and an additive selected from barium sulfate, bismuth subcarbonate, bismuth oxychloride, a polyolefin elastomer, a thermoplastics elastomer, and a mixture thereof in an amount of about 10% to about 90% by weight. In one embodiment, the stent has a density of lower than about 1.0 g/cm$^3$. In one embodiment, the stent has a density of between about 0.933 to about 0.952 g/cm$^3$. In one embodiment, the stent has a Vicat Softening temperature of about 39 to about 82° C. In one embodiment, the stent has a Vicat Softening temperature of about 45° C. In one embodiment, the stent has a tensile stress of about 11 to about 26 MPa. In one embodiment, the stent has a tensile stress of about 20 MPa. In one embodiment, the stent has an elastic modulus of about 15 to about 123 MPa. In one embodiment, the stent has an elastic modulus of about 50 MPa. In all the above embodiments, the stent may be a ureteral stent. In one embodiment, the ureteral stent may have multiple polymeric layers such as inner layer and outer layer with each layer having different elastic modulus. In one embodiment, the inner layer may have an elastic modulus of about 0.5 to about 50 MPa. In one embodiment, the outer layer may have an elastic modulus of about 100 to about 200 MPa. In one embodiment, the outer layer may have an elastic modulus of about 150 MPa. In one embodiment, the ureteral stent may have a radial gradual elastic modulus or an intermittent elastic modulus. In one embodiment, the ureteral stent may have a transitional elastic modulus along its axial direction from 0.5 cm to 40 cm with the whole ureteral stent length of about 40 cm.

In one embodiment, the present disclosure provides a stent comprising ethylene-vinyl acetate in an amount of about 9% to about 40% by weight, and an additive selected from barium sulfate, bismuth subcarbonate, bismuth oxychloride, a polyolefin elastomer, a thermoplastics elastomer, and a mixture thereof in an amount of about 30% to about 50% by weight. In one embodiment, the stent has a density of lower than about 1.0 g/cm$^3$. In one embodiment, the stent has a density of between about 0.933 to about 0.952 g/cm$^3$. In one embodiment, the stent has a Vicat Softening temperature of about 39 to about 82° C. In one embodiment, the stent has a Vicat Softening temperature of about 45° C. In one embodiment, the stent has a tensile stress of about 11 to about 26 MPa. In one embodiment, the stent has a tensile stress of about 20 MPa. In one embodiment, the stent has an elastic modulus of about 15 to about 123 MPa. In one embodiment, the stent has an elastic modulus of about 50 MPa. In all the above embodiments, the stent may be a ureteral stent. In one embodiment, the ureteral stent may have multiple polymeric layers such as inner layer and outer layer with each layer having different elastic modulus. In one embodiment, the inner layer may have an elastic modulus of about 0.5 to about 50 MPa. In one embodiment, the outer layer may have an elastic modulus of about 100 to about 200 MPa. In one embodiment, the outer layer may have an elastic modulus of about 150 MPa. In one embodiment, the ureteral stent may have a radial gradual elastic modulus or an intermittent elastic modulus. In one embodiment, the ureteral stent may have a transitional elastic modulus along its axial direction from 0.5 cm to 40 cm with the whole ureteral stent length of about 40 cm.

In one embodiment, the present disclosure provides a stent comprising ethylene-vinyl acetate in an amount of about 9% to about 40% by weight, and an additive selected from barium sulfate, bismuth subcarbonate, bismuth oxychloride, a polyolefin elastomer, a thermoplastics elastomer, and a mixture thereof in an amount of about 35% to about 45% by weight. In one embodiment, the stent has a density of lower than about 1.0 g/cm$^3$. In one embodiment, the stent has a density of between about 0.933 to about 0.952 g/cm$^3$. In one embodiment, the stent has a Vicat Softening temperature of about 39 to about 82° C. In one embodiment, the stent has a Vicat Softening temperature of about 45° C. In one embodiment, the stent has a tensile stress of about 11 to about 26 MPa. In one embodiment, the stent has a tensile stress of about 20 MPa. In one embodiment, the stent has an elastic modulus of about 15 to about 123 MPa. In one embodiment, the stent has an elastic modulus of about 50 MPa. In all the above embodiments, the stent may be a ureteral stent. In one embodiment, the ureteral stent may have multiple polymeric layers such as inner layer and outer layer with each layer having different elastic modulus. In one embodiment, the inner layer may have an elastic modulus of about 0.5 to about 50 MPa. In one embodiment, the outer layer may have an elastic modulus of about 100 to about 200 MPa. In one embodiment, the outer layer may have an elastic modulus of about 150 MPa. In one embodiment, the ureteral stent may have a radial gradual elastic modulus or an intermittent elastic modulus. In one embodiment, the ureteral stent may have a transitional elastic modulus along its axial direction from 0.5 cm to 40 cm with the whole ureteral stent length of about 40 cm.

In one embodiment, the present disclosure provides a stent comprising ethylene-vinyl acetate in an amount of about 9% to about 40% by weight, and an additive selected from barium sulfate, bismuth subcarbonate, bismuth oxychloride, a polyolefin elastomer, a thermoplastics elastomer, and a mixture thereof in an amount of about 40% by weight. In one embodiment, the stent has a density of lower than about 1.0 g/cm$^3$. In one embodiment, the stent has a density of between about 0.933 to about 0.952 g/cm$^3$. In one embodiment, the stent has a Vicat Softening temperature of about 39 to about 82° C. In one embodiment, the stent has a Vicat Softening temperature of about 45° C. In one embodiment, the stent has a tensile stress of about 11 to about 26 MPa. In one embodiment, the stent has a tensile stress of about 20 MPa. In one embodiment, the stent has an elastic modulus of about 15 to about 123 MPa. In one embodiment, the stent has an elastic modulus of about 50 MPa. In all the above embodiments, the stent may be a ureteral stent. In one embodiment, the ureteral stent may have multiple polymeric layers such as inner layer and outer layer with each layer having different elastic modulus. In one embodiment, the inner layer may have an elastic modulus of about 0.5 to about 50 MPa. In one embodiment, the outer layer may have an elastic modulus of about 100 to about 200 MPa. In one embodiment, the outer layer may have an elastic modulus of about 150 MPa. In one embodiment, the ureteral stent may have a radial gradual elastic modulus or an intermittent elastic modulus. In one embodiment, the ureteral stent may have a transitional elastic modulus along its axial direction from 0.5 cm to 40 cm with the whole ureteral stent length of about 40 cm.

In one embodiment, the disclosure provides a stent comprising ethylene-vinyl acetate in an amount of about 10% to about 30% by weight, and an additive selected from barium sulfate, bismuth subcarbonate, bismuth oxychloride, a polyolefin elastomer, a thermoplastics elastomer, and a mixture thereof in an amount of about 10% to about 90% by weight. In one embodiment, the stent has a density of lower than about 1.0 g/cm$^3$. In one embodiment, the stent has a density of between about 0.933 to about 0.952 g/cm$^3$. In one embodiment, the stent has a Vicat Softening temperature of about 39 to about 82° C. In one embodiment, the stent has a Vicat Softening temperature of about 45° C. In one embodiment, the stent has a tensile stress of about 11 to about 26 MPa. In one embodiment, the stent has a tensile stress of about 20 MPa. In one embodiment, the stent has an elastic modulus of about 15 to about 123 MPa. In one embodiment, the stent has an elastic modulus of about 50 MPa. In all the above embodiments, the stent may be a ureteral stent. In one embodiment, the ureteral stent may have multiple polymeric layers such as inner layer and outer layer with each layer having different elastic modulus. In one embodiment, the inner layer may have an elastic modulus of about 0.5 to about 50 MPa. In one embodiment, the outer layer may have an elastic modulus of about 100 to about 200 MPa. In one embodiment, the outer layer may have an elastic modulus of about 150 MPa. In one embodiment, the ureteral stent may have a radial gradual elastic modulus or an intermittent elastic modulus. In one embodiment, the ureteral stent may have a transitional elastic modulus along its axial direction from 0.5 cm to 40 cm with the whole ureteral stent length of about 40 cm.

In one embodiment, the disclosure provides a stent comprising ethylene-vinyl acetate in an amount of about 10% to about 30% by weight, and an additive selected from barium sulfate, bismuth subcarbonate, bismuth oxychloride, a polyolefin elastomer, a thermoplastics elastomer, and a mixture thereof in an amount of about 30% to about 50% by weight. In one embodiment, the stent has a density of lower than about 1.0 g/cm$^3$. In one embodiment, the stent has a density of between about 0.933 to about 0.952 g/cm$^3$. In one embodiment, the stent has a Vicat Softening temperature of about 39 to about 82° C. In one embodiment, the stent has a Vicat Softening temperature of about 45° C. In one embodiment, the stent has a tensile stress of about 11 to about 26 MPa. In one embodiment, the stent has a tensile stress of about 20 MPa. In one embodiment, the stent has an elastic modulus of about 15 to about 123 MPa. In one embodiment, the stent has an elastic modulus of about 50 MPa. In all the above embodiments, the stent may be a ureteral stent. In one embodiment, the ureteral stent may have multiple polymeric layers such as inner layer and outer layer with each layer having different elastic modulus. In one embodiment, the inner layer may have an elastic modulus of about 0.5 to about 50 MPa. In one embodiment, the outer layer may have an elastic modulus of about 100 to about 200 MPa. In one embodiment, the outer layer may have an elastic modulus of about 150 MPa. In one embodiment, the ureteral stent may have a radial gradual elastic modulus or an intermittent elastic modulus. In one embodiment, the ureteral stent may have a transitional elastic modulus along its axial direction from 0.5 cm to 40 cm with the whole ureteral stent length of about 40 cm.

In one embodiment, the disclosure provides a stent comprising ethylene-vinyl acetate in an amount of about 10% to about 30% by weight, and an additive selected from barium sulfate, bismuth subcarbonate, bismuth oxychloride, a polyolefin elastomer, a thermoplastics elastomer, and a mixture thereof in an amount of about 35% to about 45% by weight. In one embodiment, the stent has a density of lower than about 1.0 g/cm$^3$. In one embodiment, the stent has a density of between about 0.933 to about 0.952 g/cm$^3$. In one embodiment, the stent has a Vicat Softening temperature of about 39 to about 82° C. In one embodiment, the stent has a Vicat Softening temperature of about 45° C. In one embodiment, the stent has a tensile stress of about 11 to about 26 MPa. In one embodiment, the stent has a tensile stress of about 20 MPa. In one embodiment, the stent has an elastic modulus of about 15 to about 123 MPa. In one embodiment, the stent has an elastic modulus of about 50 MPa. In all the above embodiments, the stent may be a ureteral stent. In one embodiment, the ureteral stent may have multiple polymeric layers such as inner layer and outer layer with each layer having different elastic modulus. In one embodiment, the inner layer may have an elastic modulus of about 0.5 to about 50 MPa. In one embodiment, the outer layer may have an elastic modulus of about 100 to about 200 MPa. In one embodiment, the outer layer may have an elastic modulus of about 150 MPa. In one embodiment, the ureteral stent may have a radial gradual elastic modulus or an intermittent elastic modulus. In one embodiment, the ureteral stent may have a transitional elastic modulus along its axial direction from 0.5 cm to 40 cm with the whole ureteral stent length of about 40 cm.

In one embodiment, the disclosure provides a stent comprising ethylene-vinyl acetate in an amount of about 10% to about 30% by weight, and an additive selected from barium sulfate, bismuth subcarbonate, bismuth oxychloride, a polyolefin elastomer, a thermoplastics elastomer, and a mixture thereof in an amount of about 40% by weight. In one embodiment, the stent has a density of lower than about 1.0 g/cm$^3$. In one embodiment, the stent has a density of between about 0.933 to about 0.952 g/cm$^3$. In one embodiment, the stent has a Vicat Softening temperature of about 39 to about 82° C. In one embodiment, the stent has a Vicat Softening temperature of about 45° C. In one embodiment, the stent has a tensile stress of about 11 to about 26 MPa. In one embodiment, the stent has a tensile stress of about 20 MPa. In one embodiment, the stent has an elastic modulus of about 15 to about 123 MPa. In one embodiment, the stent has an elastic modulus of about 50 MPa. In all the above embodiments, the stent may be a ureteral stent. In one embodiment, the ureteral stent may have multiple polymeric layers such as inner layer and outer layer with each layer having different elastic modulus. In one embodiment, the inner layer may have an elastic modulus of about 0.5 to about 50 MPa. In one embodiment, the outer layer may have an elastic modulus of about 100 to about 200 MPa. In one embodiment, the outer layer may have an elastic modulus of about 150 MPa. In one embodiment, the ureteral stent may have a radial gradual elastic modulus or an intermittent elastic modulus. In one embodiment, the ureteral stent may have a transitional elastic modulus along its axial direction from 0.5 cm to 40 cm with the whole ureteral stent length of about 40 cm.

In one embodiment, the disclosure provides a stent comprising ethylene-vinyl acetate in an amount of about 15% to about 25% by weight, and an additive selected from barium sulfate, bismuth subcarbonate, bismuth oxychloride, a polyolefin elastomer, a thermoplastics elastomer, and a mixture thereof in an amount of about 10% to about 85% by weight. In one embodiment, the stent has a density of lower than about 1.0 g/cm$^3$. In one embodiment, the stent has a density of between about 0.933 to about 0.952 g/cm$^3$. In one embodiment, the stent has a Vicat Softening temperature of about 39 to about 82° C. In one embodiment, the stent has a Vicat Softening temperature of about 45° C. In one embodiment, the stent has a tensile stress of about 11 to about 26 MPa. In one embodiment, the stent has a tensile stress of about 20 MPa. In one embodiment, the stent has an elastic modulus of about 15 to about 123 MPa. In one embodiment, the stent has an elastic modulus of about 50 MPa. In all the above embodiments, the stent may be a ureteral stent. In one embodiment, the ureteral stent may have multiple polymeric layers such as inner layer and outer layer with each layer having different elastic modulus. In one embodiment, the inner layer may have an elastic modulus of about 0.5 to about 50 MPa. In one embodiment, the outer layer may have an elastic modulus of about 100 to about 200 MPa. In one embodiment, the outer layer may have an elastic modulus of about 150 MPa. In one embodiment, the ureteral stent may have a radial gradual elastic modulus or an intermittent elastic modulus. In one embodiment, the ureteral stent may have a transitional elastic modulus along its axial direction from 0.5 cm to 40 cm with the whole ureteral stent length of about 40 cm.

In one embodiment, the disclosure provides a stent comprising ethylene-vinyl acetate in an amount of about 15% to about 25% by weight, and an additive selected from barium sulfate, bismuth subcarbonate, bismuth oxychloride, a polyolefin elastomer, a thermoplastics elastomer, and a mixture thereof in an amount of about 30% to about 50% by weight. In one embodiment, the stent has a density of lower than about 1.0 g/cm$^3$. In one embodiment, the stent has a density of between about 0.933 to about 0.952 g/cm$^3$. In one embodiment, the stent has a Vicat Softening temperature of about 39 to about 82° C. In one embodiment, the stent has a Vicat Softening temperature of about 45° C. In one embodiment, the stent has a tensile stress of about 11 to about 26 MPa. In one embodiment, the stent has a tensile stress of about 20 MPa. In one embodiment, the stent has an elastic modulus of about 15 to about 123 MPa. In one embodiment, the stent has an elastic modulus of about 50 MPa. In all the above embodiments, the stent may be a ureteral stent. In one embodiment, the ureteral stent may have multiple polymeric layers such as inner layer and outer layer with each layer having different elastic modulus. In one embodiment, the inner layer may have an elastic modulus of about 0.5 to about 50 MPa. In one embodiment, the outer layer may have an elastic modulus of about 100 to about 200 MPa. In one embodiment, the outer layer may have an elastic modulus of about 150 MPa. In one embodiment, the ureteral stent may have a radial gradual elastic modulus or an intermittent elastic modulus. In one embodiment, the ureteral stent may have a transitional elastic modulus along its axial direction from 0.5 cm to 40 cm with the whole ureteral stent length of about 40 cm.

In one embodiment, the disclosure provides a stent comprising ethylene-vinyl acetate in an amount of about 15% to about 25% by weight, and an additive selected from barium sulfate, bismuth subcarbonate, bismuth oxychloride, a polyolefin elastomer, a thermoplastics elastomer, and a mixture thereof in an amount of about 35% to about 45% by weight. In one embodiment, the stent has a density of lower than about 1.0 g/cm$^3$. In one embodiment, the stent has a density of between about 0.933 to about 0.952 g/cm$^3$. In one embodiment, the stent has a Vicat Softening temperature of about 39 to about 82° C. In one embodiment, the stent has a Vicat Softening temperature of about 45° C. In one embodiment, the stent has a tensile stress of about 11 to about 26 MPa. In one embodiment, the stent has a tensile stress of about 20 MPa. In one embodiment, the stent has an elastic modulus of about 15 to about 123 MPa. In one embodiment, the stent has an elastic modulus of about 50 MPa. In all the above embodiments, the stent may be a ureteral stent. In one embodiment, the ureteral stent may have multiple polymeric layers such as inner layer and outer layer with each layer having different elastic modulus. In one embodiment, the inner layer may have an elastic modulus of about 0.5 to about 50 MPa. In one embodiment, the outer layer may have an elastic modulus of about 100 to about 200 MPa. In one embodiment, the outer layer may have an elastic modulus of about 150 MPa. In one embodiment, the ureteral stent may have a radial gradual elastic modulus or an intermittent elastic modulus. In one embodiment, the ureteral stent may have a transitional elastic modulus along its axial direction from 0.5 cm to 40 cm with the whole ureteral stent length of about 40 cm.

In one embodiment, the disclosure provides a stent comprising ethylene-vinyl acetate in an amount of about 15% to about 25% by weight, and an additive selected from barium sulfate, bismuth subcarbonate, bismuth oxychloride, a polyolefin elastomer, a thermoplastics elastomer, and a mixture thereof in an amount of about 40% by weight. In one embodiment, the stent has a density of lower than about 1.0 g/cm³. In one embodiment, the stent has a density of between about 0.933 to about 0.952 g/cm³. In one embodiment, the stent has a Vicat Softening temperature of about 39 to about 82° C. In one embodiment, the stent has a Vicat Softening temperature of about 45° C. In one embodiment, the stent has a tensile stress of about 11 to about 26 MPa. In one embodiment, the stent has a tensile stress of about 20 MPa. In one embodiment, the stent has an elastic modulus of about 15 to about 123 MPa. In one embodiment, the stent has an elastic modulus of about 50 MPa. In all the above embodiments, the stent may be a ureteral stent. In one embodiment, the ureteral stent may have multiple polymeric layers such as inner layer and outer layer with each layer having different elastic modulus. In one embodiment, the inner layer may have an elastic modulus of about 0.5 to about 50 MPa. In one embodiment, the outer layer may have an elastic modulus of about 100 to about 200 MPa. In one embodiment, the outer layer may have an elastic modulus of about 150 MPa. In one embodiment, the ureteral stent may have a radial gradual elastic modulus or an intermittent elastic modulus. In one embodiment, the ureteral stent may have a transitional elastic modulus along its axial direction from 0.5 cm to 40 cm with the whole ureteral stent length of about 40 cm.

In one embodiment, the disclosure provides a stent comprising ethylene-vinyl acetate in an amount of about 24% by weight, and an additive selected from barium sulfate, bismuth subcarbonate, bismuth oxychloride, a polyolefin elastomer, a thermoplastics elastomer, and a mixture thereof in an amount of about 10% to about 76% by weight. In one embodiment, the stent has a density of lower than about 1.0 g/cm³. In one embodiment, the stent has a density of between about 0.933 to about 0.952 g/cm³. In one embodiment, the stent has a Vicat Softening temperature of about 39 to about 82° C. In one embodiment, the stent has a Vicat Softening temperature of about 45° C. In one embodiment, the stent has a tensile stress of about 11 to about 26 MPa. In one embodiment, the stent has a tensile stress of about 20 MPa. In one embodiment, the stent has an elastic modulus of about 15 to about 123 MPa. In one embodiment, the stent has an elastic modulus of about 50 MPa. In all the above embodiments, the stent may be a ureteral stent. In one embodiment, the ureteral stent may have multiple polymeric layers such as inner layer and outer layer with each layer having different elastic modulus. In one embodiment, the inner layer may have an elastic modulus of about 0.5 to about 50 MPa. In one embodiment, the outer layer may have an elastic modulus of about 100 to about 200 MPa. In one embodiment, the outer layer may have an elastic modulus of about 150 MPa. In one embodiment, the ureteral stent may have a radial gradual elastic modulus or an intermittent elastic modulus. In one embodiment, the ureteral stent may have a transitional elastic modulus along its axial direction from 0.5 cm to 40 cm with the whole ureteral stent length of about 40 cm.

In one embodiment, the disclosure provides a stent comprising ethylene-vinyl acetate in an amount of about 24% by weight, and an additive selected from barium sulfate, bismuth subcarbonate, bismuth oxychloride, a polyolefin elastomer, a thermoplastics elastomer, and a mixture thereof in an amount of about 30% to about 50% by weight. In one embodiment, the stent has a density of lower than about 1.0 g/cm³. In one embodiment, the stent has a density of between about 0.933 to about 0.952 g/cm³. In one embodiment, the stent has a Vicat Softening temperature of about 39 to about 82° C. In one embodiment, the stent has a Vicat Softening temperature of about 45° C. In one embodiment, the stent has a tensile stress of about 11 to about 26 MPa. In one embodiment, the stent has a tensile stress of about 20 MPa. In one embodiment, the stent has an elastic modulus of about 15 to about 123 MPa. In one embodiment, the stent has an elastic modulus of about 50 MPa. In all the above embodiments, the stent may be a ureteral stent. In one embodiment, the ureteral stent may have multiple polymeric layers such as inner layer and outer layer with each layer having different elastic modulus. In one embodiment, the inner layer may have an elastic modulus of about 0.5 to about 50 MPa. In one embodiment, the outer layer may have an elastic modulus of about 100 to about 200 MPa. In one embodiment, the outer layer may have an elastic modulus of about 150 MPa. In one embodiment, the ureteral stent may have a radial gradual elastic modulus or an intermittent elastic modulus. In one embodiment, the ureteral stent may have a transitional elastic modulus along its axial direction from 0.5 cm to 40 cm with the whole ureteral stent length of about 40 cm.

In one embodiment, the disclosure provides a stent comprising ethylene-vinyl acetate in an amount of about 24% by weight, and an additive selected from barium sulfate, bismuth subcarbonate, bismuth oxychloride, a polyolefin elastomer, a thermoplastics elastomer, and a mixture thereof in an amount of about 35% to about 45% by weight. In one embodiment, the stent has a density of lower than about 1.0 g/cm³. In one embodiment, the stent has a density of between about 0.933 to about 0.952 g/cm³. In one embodiment, the stent has a Vicat Softening temperature of about 39 to about 82° C. In one embodiment, the stent has a Vicat Softening temperature of about 45° C. In one embodiment, the stent has a tensile stress of about 11 to about 26 MPa. In one embodiment, the stent has a tensile stress of about 20 MPa. In one embodiment, the stent has an elastic modulus of about 15 to about 123 MPa. In one embodiment, the stent has an elastic modulus of about 50 MPa. In all the above embodiments, the stent may be a ureteral stent. In one embodiment, the ureteral stent may have multiple polymeric layers such as inner layer and outer layer with each layer having different elastic modulus. In one embodiment, the inner layer may have an elastic modulus of about 0.5 to about 50 MPa. In one embodiment, the outer layer may have an elastic modulus of about 100 to about 200 MPa. In one embodiment, the outer layer may have an elastic modulus of about 150 MPa. In one embodiment, the ureteral stent may have a radial gradual elastic modulus or an intermittent elastic modulus. In one embodiment, the ureteral stent may have a transitional elastic modulus along its axial direction from 0.5 cm to 40 cm with the whole ureteral stent length of about 40 cm.

In one embodiment, the disclosure provides a stent comprising ethylene-vinyl acetate in an amount of about 24% by weight, and an additive selected from barium sulfate, bismuth subcarbonate, bismuth oxychloride, a polyolefin elastomer, a thermoplastics elastomer, and a mixture thereof in an amount of about 40% by weight. In one embodiment, the stent has a density of lower than about 1.0 g/cm³. In one embodiment, the stent has a density of between about 0.933 to about 0.952 g/cm³. In one embodiment, the stent has a Vicat Softening temperature of about 39 to about 82° C. In one embodiment, the stent has a Vicat Softening temperature of about 45° C. In one embodiment, the stent has a tensile stress of about 11 to about 26 MPa. In one embodiment, the stent has a tensile stress of about 20 MPa. In one embodiment, the stent has an elastic modulus of about 15 to about 123 MPa. In one embodiment, the stent has an elastic modulus of about 50 MPa. In all the above embodiments, the stent may be a ureteral stent. In one embodiment, the ureteral stent may have multiple polymeric layers such as inner layer and outer layer with each layer having different elastic modulus. In one embodiment, the inner layer may have an elastic modulus of about 0.5 to about 50 MPa. In one embodiment, the outer layer may have an elastic modulus of about 100 to about 200 MPa. In one embodiment, the outer layer may have an elastic modulus of about 150 MPa. In one embodiment, the ureteral stent may have a radial gradual elastic modulus or an intermittent elastic modulus. In one embodiment, the ureteral stent may have a transitional elastic modulus along its axial direction from 0.5 cm to 40 cm with the whole ureteral stent length of about 40 cm.

A stent of the present disclosure may be made partially or completely from a biodegradable, bioresorbable, and bioabsorbable polymer or polymers. The stent may also be made in part of a biostable polymer. A polymer for use in fabricating a stent may be biostable, bioresorbable, bioabsorbable, biodegradable, or bioerodible. Biostable refers to polymers that are not biodegradable. The terms biodegradable, bioresorbable, bioabsorbable, and bioerodible are used interchangeably and refer to polymers that are capable of being completely degraded and/or eroded into different degrees of molecular levels when exposed to bodily fluids such as blood and can be gradually resorbed, absorbed, and/or eliminated by the body. The processes of breaking down and absorption of the polymer can be caused by, for example, hydrolysis and metabolic processes.

Bioabsorbable stents can be useful for treatment of various types of bodily lumens. In general, these treatments require the stent to provide mechanical support for a certain period of time and then desirably to absorb away and disappear from the implant site. The important properties of a bioabsorbable stent or scaffolding include mechanical and degradation properties. The mechanical requirements include high radial strength, high radial stiffness, and high fracture toughness. The degradation properties include the repeatable absorption profile, for example, the change in molecular weight, radial strength, and mass with time.

A scaffold made from a bioabsorbable polymer may be designed to maintain its radial strength once implanted to provide mechanical support and maintain patency of the lumen. The radial strength must be sufficiently high initially to support the lumen at an expanded or desired diameter. The period of time that the scaffolding is required or desired to maintain patency depends on the type of treatment. Therefore, after this time period, the scaffolding may start to lose radial strength due to molecular weight degradation. As the scaffolding degrades further, it starts to lose mechanical integrity and then experiences mass loss and eventually absorbs away completely or there are negligible traces left behind.

Ideally, it is desired that once the stent support is no longer needed by the lumen, the bioabsorbable scaffold is absorbed as fast as possible while also meeting all basic safety requirements during its degradation period. Such safety requirements can include a gradual disintegration and resorption that does not allow release of fragments that could cause adverse events such as thrombosis.

The mechanical requirements of bioabsorbable scaffolding include high radial strength, high stiffness or high modulus, and high fracture toughness. With respect to radial strength and stiffness, a stent should have sufficient radial strength to withstand structural loads, namely radial compressive forces, imposed on the stent so that the stent can supports the walls of a lumen such as a ureter at a selected diameter for a desired time period. A polymeric stent with adequate radial strength and/or stiffness enables the stent to maintain a lumen at a desired diameter for a sufficient period of time after implantation into the body lumen.

In addition, the stent should possess sufficient toughness or resistance to fracture to allow for crimping, expansion, and cyclic loading without fracture or cracking that would compromise the function of the stent. The toughness or resistance to fracture can be characterized for a material by the elongation at break and for a stent by the number and degree of cracks in a scaffold after use, (especially in the rings), such as after crimping or deployment. These aspects of the use of the stent involve deformation of various hinge portions of the structural elements of the scaffolding.

In one embodiment, the present disclosure also provides a method of making a comfort stent through multilayer tubing co-extrusion in combination with advanced micro-extrusion technologies. More particularly, the ureteral stents are made through the melt process of polymer compounding, and the functional additives may also be added to enhance or modify the properties of the ureteral stents.

In another embodiment, the present disclosure further provides a method of treating a kidney or a bladder related condition in a subject, the method comprising placing a comfort stent disclosed herein into a site of a subject that needs treatment through the known procedures. The treatment method may be in combination with other treatment methods or therapeutic agents.

EXAMPLES

Example 1: Comfort Ureteral Stent Materials

Comfort ureteral stents were made through the melt process of polymer compounding. Functional additives were added to the polyolefin elastomers mixture to enhance or change the properties of the resultant comfort ureteral stent materials including adjusting the suitable thermo-response as well as the softness of the stent materials. In this study, the functional additives were used to improve some of the other desired properties such as reduced thermo-oxidative degradation during polymer melt processing and extended in vivo bio-degradation time frame for stent long term application.

TABLE 1

Comfort Stent Materials

| Formulation | POE[1] | POE[2] | Functional Additive[3] | Functional Additive[4] | Functional Additive[5] | Functional Additive[6] |
|---|---|---|---|---|---|---|
| TH1 | 80% | 0% | 15-20% | 0% | 0% | <5% |
| TH2 | 60% | 0% | 35-40% | 0% | 0% | <5% |
| TH3 | 40% | 0% | 55-60% | 0% | 0% | <5% |
| TH4 | 80% | 0% | 0% | 15-20% | 0% | <5% |
| TH5 | 60% | 0% | 0% | 35-40% | 0% | <5% |
| TH6 | 40% | 0% | 0% | 55-60% | 0% | <5% |
| TH7 | 80% | 0% | 0% | 0% | 15-20% | <5% |
| TH8 | 60% | 0% | 0% | 0% | 35-40% | <5% |
| TH9 | 40% | 0% | 0% | 0% | 55-60% | <5% |
| TH10 | 0% | 80% | 15-20% | 0% | 0% | <5% |
| TH11 | 0% | 60% | 35-40% | 0% | 0% | <5% |
| TH12 | 0% | 40% | 55-60% | 0% | 0% | <5% |
| TH13 | 0% | 80% | 0% | 15-20% | 0% | <5% |
| TH14 | 0% | 60% | 0% | 35-40% | 0% | <5% |
| TH15 | 0% | 40% | 0% | 55-60% | 0% | <5% |
| TH16 | 0% | 80% | 0% | 0% | 15-20% | <5% |

TABLE 1-continued

Comfort Stent Materials

| Formulation | POE[1] | POE[2] | Functional Additive[3] | Functional Additive[4] | Functional Additive[5] | Functional Additive[6] |
|---|---|---|---|---|---|---|
| TH17 | 0% | 60% | 0% | 0% | 35-40% | <5% |
| TH18 | 0% | 40% | 0% | 0% | 55-60% | <5% |

1. POE[1] and POE[2] are polyolefin elastomers with different shore A durometer including but not limited, ethylene-vinyl acetate (EVA), thermoplastic polyolefin elastomers and so on;
2. Functional Additive[3], functional additive[4] and functional[5] are inorganic additives including but not limited, $BaSO_4$, $Bi_2O_2CO_3$, BiOCl, and so on;
3. Functional additive[6] is either inorganic additives or organic additives including but not limited, $TiO_2$, pigments from FDA 21 CFR Parts 73 and 74, antioxidant agents and so on;
4. Melt Index (g/10 min, 190° C., 2.16 kg) between 0.35 and 8.4.

Example 2: Process Technology for Comfort Ureteral Stent Products

The process technology of comfort ureteral stent is below:
1. Comfort stent materials with different Shore A durometer by polymer compounding process technology;
2. Stent tubing materials with either single layer or multilayer structure by polymer extrusion process technology;
3. Stent tapering with polymer thermoforming process technology;
4. Stent coil forming with either RF thermoforming process technology or traditional thermoforming process technology;
5. Stent drainage holes with either laser technology, or traditional mechanical machining technology;
6. Stent could be coated with different coating technology either wet chemistry technology or dry chemistry technology.

Example 3: Extrusion/Co-Extrusion Process for Comfort Stent Products

The extrusion/co-extrusion process for comfort stent is below:
1. Multilayer tubing co-extrusion combining with advanced micro-extrusion technologies;
2. Three Screw zone Design: feed zone, metering zone and compression zone (compression ratio preferably 2.5:1 and 3.5:1);
3. The length to diameter ration of screw should be greater than 20:1;
4. Breaker plate should be more 250 or 400 mm (60 or 40 mesh gauges);
5. Processing temperature should from 140° C. to 210° C. but should not be over 220° C.;
6. Water cooling of the feed throat, low temperature for the rear barrel heating zone to prevent bridging, which could result partial or complete interruption of flow during extrusion;

Example 4: Testing Methods for Comfort Stent Products

According to ASTM F 1828-97 (Reapproved 2014) "Standard Specification for Ureteral Stents", test methods for comfort stent products are described below.
Break Strength Test and Elongation Description
Testing Procedure
Most stents contain drainage holes. Ideally, these stents should break at a drainage hole. This is how tensile failures typically occur in vivo. However, stent may break in locations other than drainage holes. This type of failure may be indicative of potential design or process related problems. In stents without drainage holes, this type of failure is to be expected.

Only a segment of the test stent is used for the break strength test. The grippers should be separated by 2 inch. This 2 inch segment should contain at least one drainage hole (if drainage holes are present) and should contain the section of the stent with the smallest cross sectional area or weakest point.

Elongation—The elongation of stent segments separated by 2 inch between the extensometer grips used to hold the segment in INSTRON or tow marks placed on the surface of the stent will be determined in accordance with Test Method D 412.

Place the test specimen in the grips of INSTRON, using care to adjust the specimen symmetrically to distribute tension uniformly over the cross section. This avoids complications that prevent the maximum strength of the material from being evaluated. Unless otherwise specified, the rate of grip separation shall be 20±2 in/min. (500±50 mm/min.). Start the machine and note the distance between the bench marks, taking care to avoid parallax. Record the force at the elongation specified for the test and at the time of rupture. The elongation measurement is made preferable through the use of an extensometer.
Retention Strength Test Description
Testing Procedure
The apparatus is set up as shown in FIG. 1. Clearance between the outside diameter of the stent and inside diameter of the funnel block hole must be present.

Maintain temperature in the water bath at 37±3° C. by whatever means is available to the test facility. Submerge the entire funnel block. Set the pull through the fixture at the beginning 20 in./min. Clean the test bath and fixture at the beginning of each testing day. The capacity of the load cell used with the tensile testing machine should not exceed 2 lbf (10N).

The test specimen shall consist of actual sterilized product. The specimen shall be cut to allow a straight portion of the stent to be inserted upwards through the funnel fixture into the grip of INSTRON without loading the retention mechanism of the stent to be tested. Submerge the test specimen in the water bath for at least 1 min to allow it to reach thermal equilibrium. If the material is significantly affected by moisture, allow the specimen to equilibrate for a minimum of 24 h. Use distilled water if possible.

Figure 2:
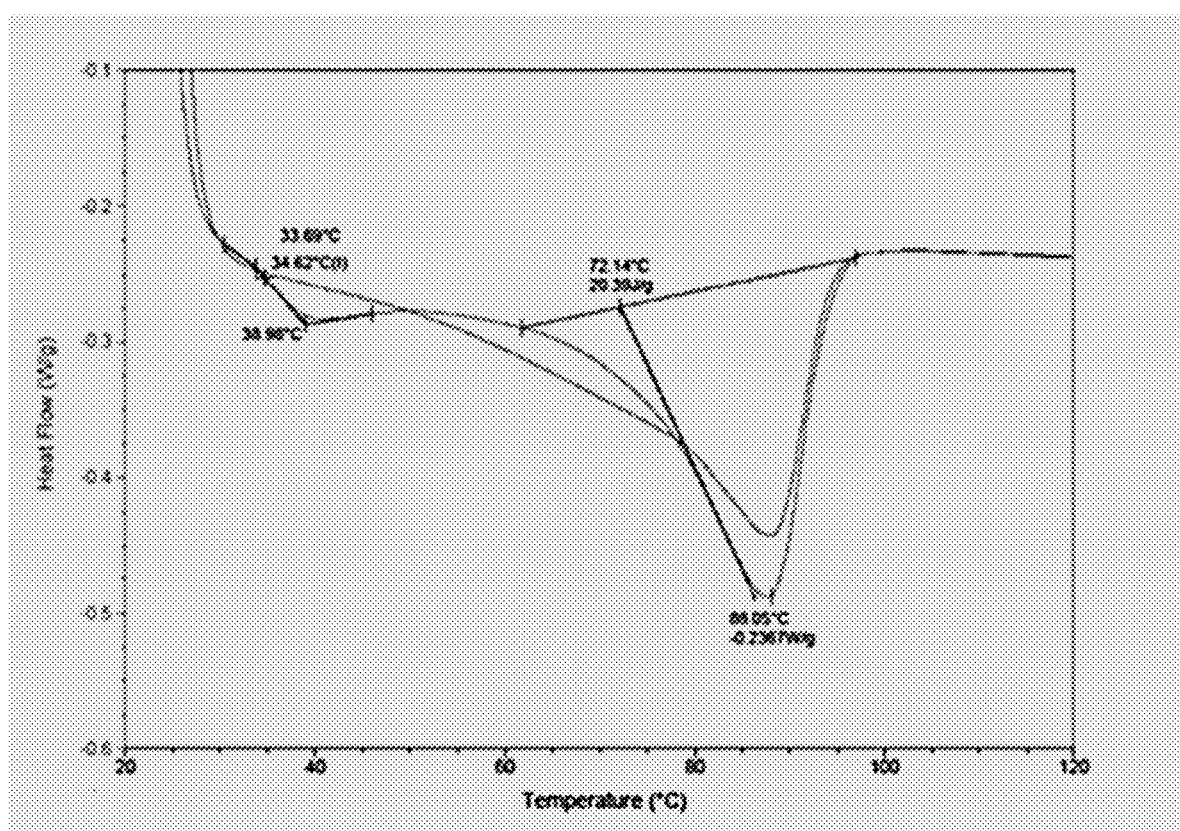
FIG. 2 shows a DSC measurement result for a stent having a formulation TH5.
Figure 3:
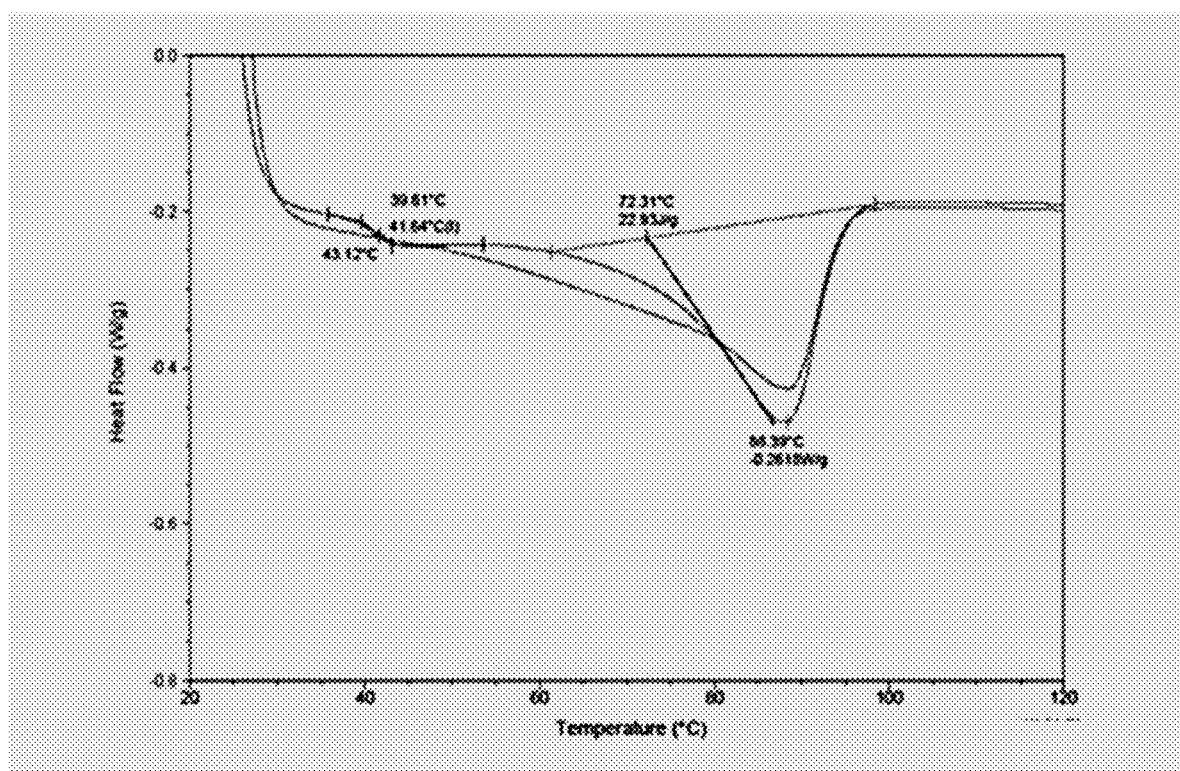
FIG. 3 shows a DSC measurement result for a stent having a formulation TH8.
Figure 4:
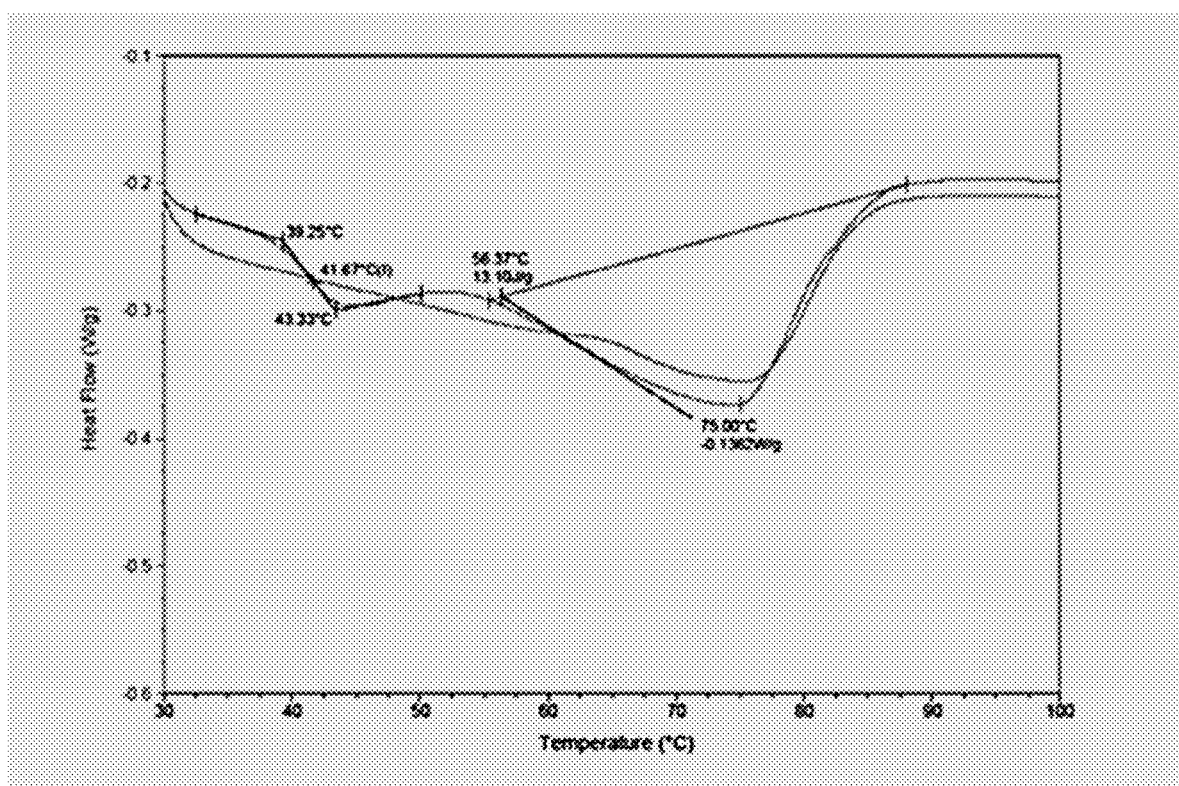
FIG. 4 shows a DSC measurement result for a stent having a formulation TH14.
Figure 5:
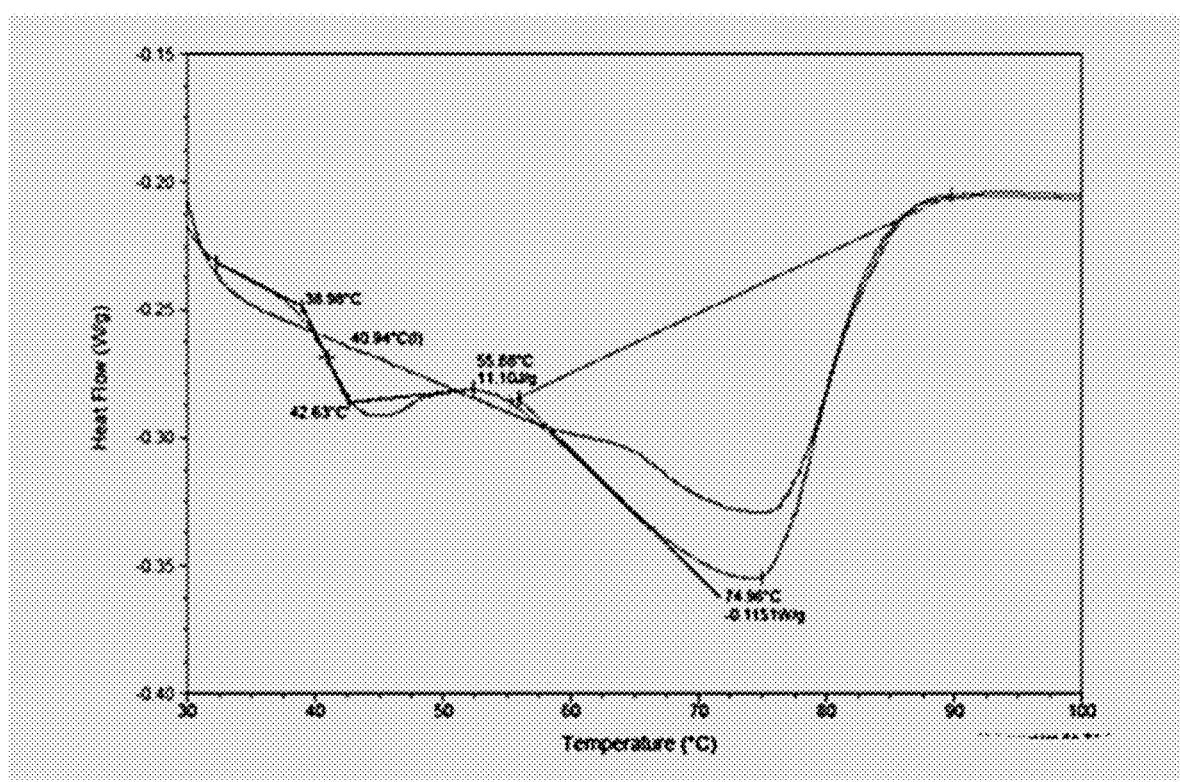
FIG. 5 shows a DSC measurement result for a stent having a formulation TH17.

Example 5: The Results of Differential Scanning Calorimetry (DSC) for Some Representative Stents DSC is a thermoanalytical technique in which the difference in the amount of heat required to increase the temperature of a sample and reference is measured as a function of temperature. Both the sample and reference are maintained at nearly the same temperature throughout the experiment. Generally, the temperature program for a DSC analysis is designed such that the sample holder temperature increases linearly as a function of time. The reference sample should have a well-defined heat capacity over the range of temperatures to be scanned. The result of a DSC experiment is a curve of heat flux versus temperature or versus time. There are two different conventions: exothermic reactions in the sample shown with a positive or negative peak, depending on the kind of technology used in the experiment. This curve can be used to calculate enthalpies of transitions. DSC is used widely for examining polymeric materials to determine their thermal transitions. The observed thermal transitions can be utilized to compare materials, although the transitions do not uniquely identify composition. The composition of unknown materials may be completed using complementary techniques such as IR spectroscopy. Melting points and glass transition temperatures for most polymers are available from standard compilations, and the method can show polymer degradation by the lowering of the expected melting point, Tm, for example. Tm depends on the molecular weight of the polymer and thermal history, so lower grades may have lower melting points than expected. The percent crystalline content of a polymer can be estimated from the crystallization/melting peaks of the DSC graph as reference heats of fusion can be found in the literature. FIGS. 2-5 show the results of DSC determination for some of the representative stents. FIG. 2 shows a DSC graph of a stent having a formulation of TH5 as indicated in Table 1 above. FIG. 3 shows that of a stent having a formulation of TH8 as indicated in Table 1. FIG. 4 shows that of a stent having a formulation of TH14 as indicated in Table 1. FIG. 5 shows that of a stent having a formulation of TH17 as indicated in Table 1. From these graphs, it can be seen that these stents all have a transition temperature around 40° C., close to body temperature. Having such a transition temperature will likely minimize the uncomfortable feeling by a patient once inserted or disposed inside the patient. As a result, they are quite suitable for insertion or disposition inside a human body. Put it another way, these stents will make a patient feel quite comfortable once disposed inside the patient body.

Figure 6:
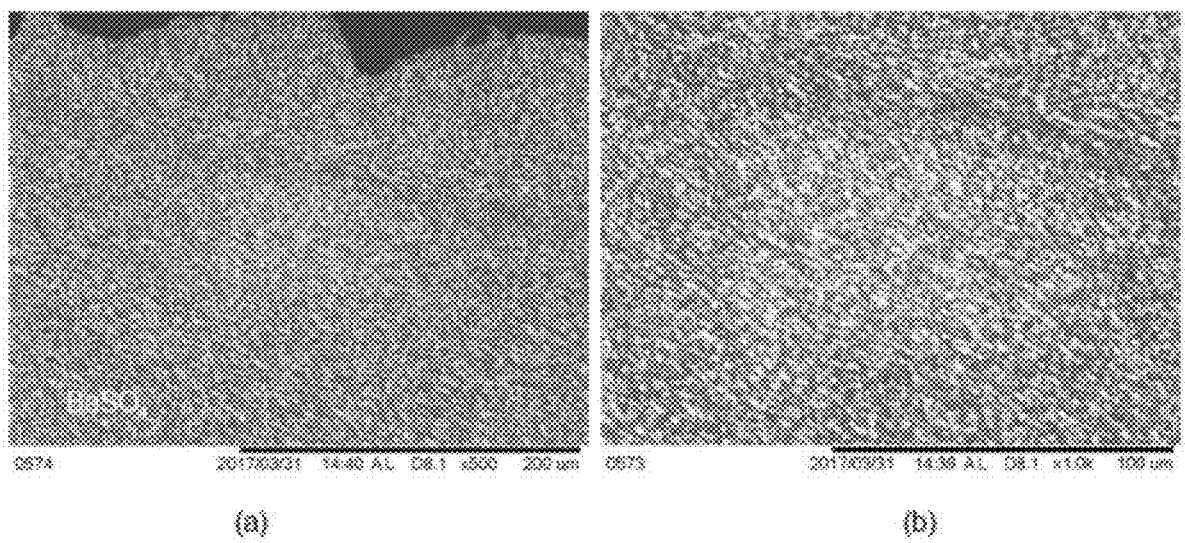
FIG. 6 shows an SEM measurement result for a stent having a formulation TH2.
Figure 7:
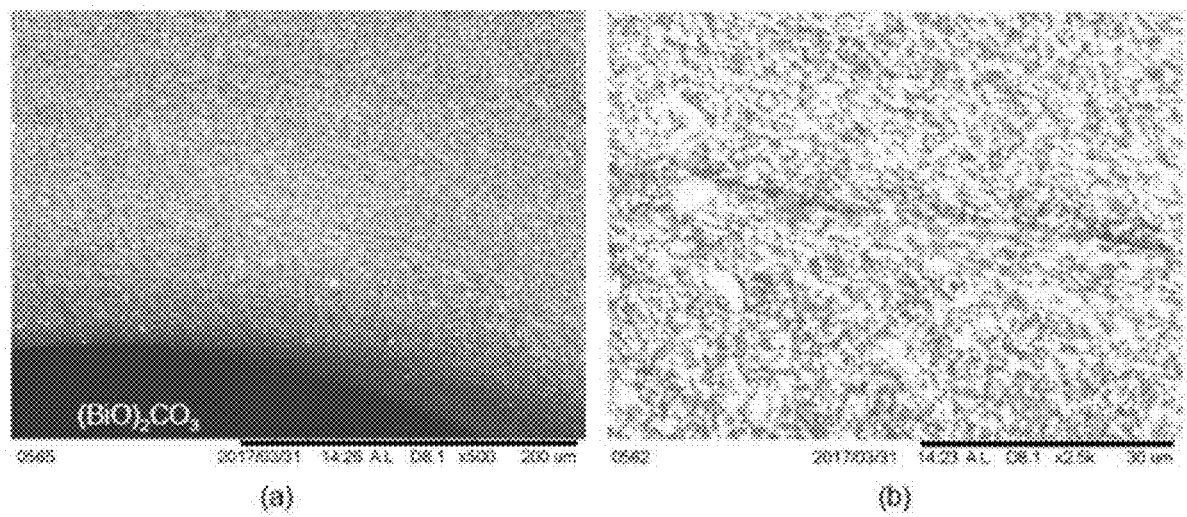
FIG. 7 shows an SEM measurement result for a stent having a formulation TH5.
Figure 8:
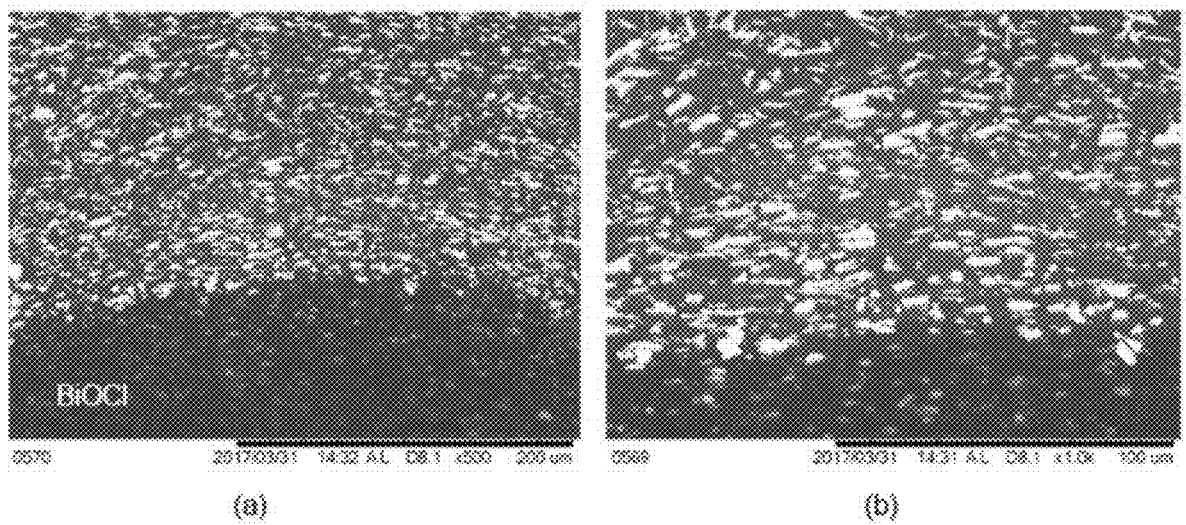
FIG. 8 shows an SEM measurement result for a stent having a formulation TH8.
Figure 9:
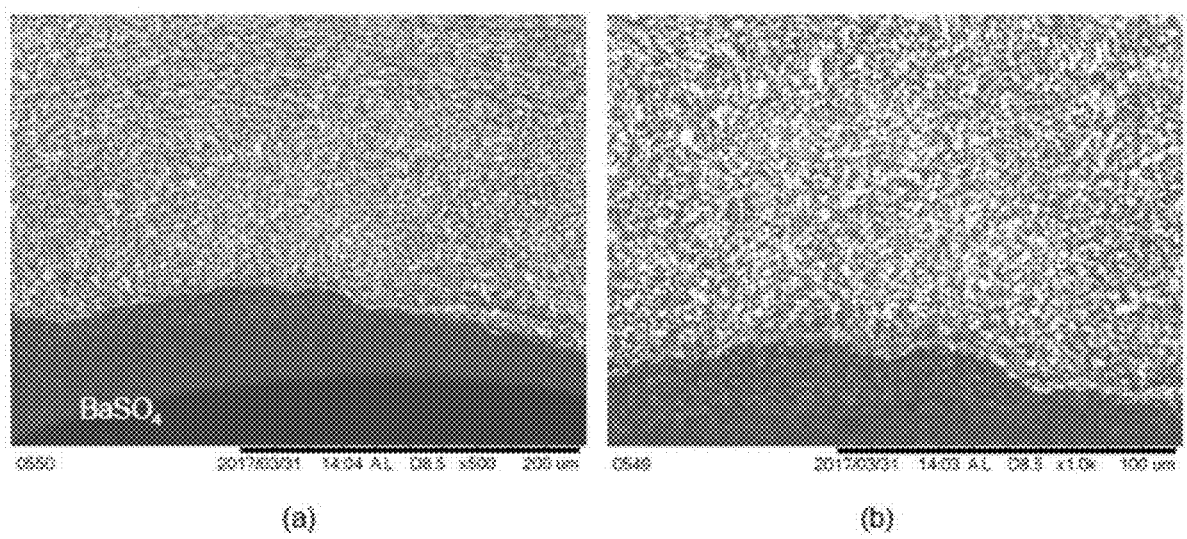
FIG. 9 shows an SEM measurement result for a stent having a formulation TH11.
Figure 10:
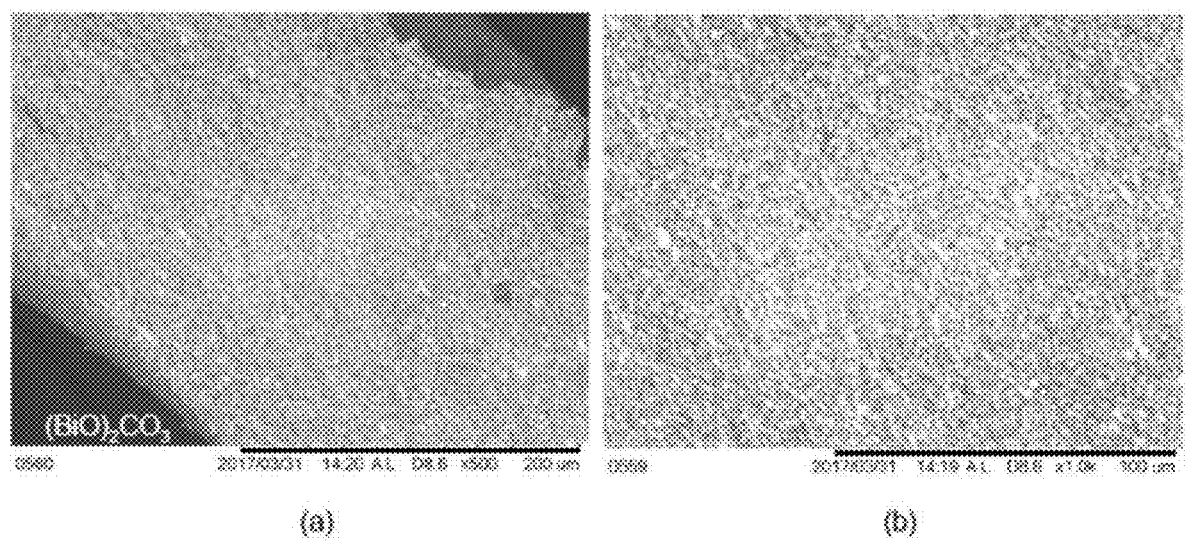
FIG. 10 shows an SEM measurement result for a stent having a formulation TH14.
Figure 11:
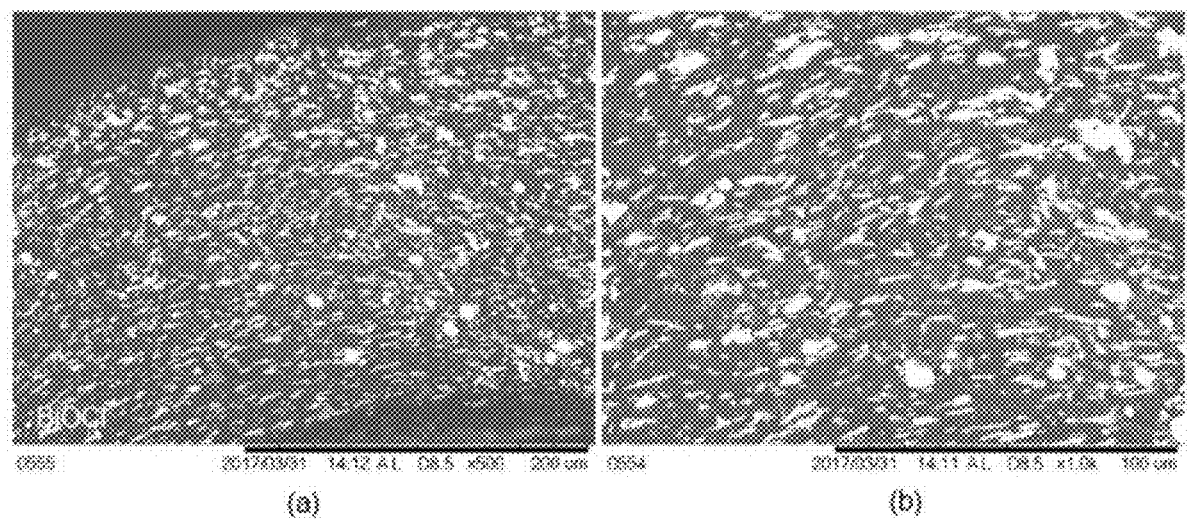
FIG. 11 shows an SEM measurement result for a stent having a formulation TH17.

Example 6: The Results of Scanning Electronic Microscopy (SEM) for Some Representative Stents A scanning electron microscope (SEM) is a type of electron microscope that produces images of a sample by scanning the surface with a focused beam of electrons. The electrons interact with atoms in the sample, producing various signals that contain information about the sample's surface topography and composition. The electron beam is scanned in a raster scan pattern, and the beam's position is combined with the detected signal to produce an image. SEM can achieve resolution better than 1 nanometer. Specimens can be observed in high vacuum in conventional SEM, or in low vacuum or wet conditions in variable pressure or environmental SEM, and at a wide range of cryogenic or elevated temperatures with specialized instruments. The most common SEM mode is detection of secondary electrons emitted by atoms excited by the electron beam. The number of secondary electrons that can be detected depends, among other things, on specimen topography. By scanning the sample and collecting the secondary electrons that are emitted using a special detector, an image displaying the topography of the surface is created. In secondary electron imaging, or SEI, the secondary electrons are emitted from very close to the specimen surface. Consequently, SEM can produce very high-resolution images of a sample surface, revealing details less than 1 nm in size. FIGS. 6-11 show the results of SEM determination for some representative stents. FIGS. 6 (*a*) and (*b*) show the SEM imaging result of a stent having a formulation of TH2 as indicated in Table 1 (FIG. 6 (*b*) is just an enlargement of FIG. 6 (*a*); This applies to the situations for FIGS. 6-11). FIGS. 7 (*a*) and (*b*) show the SEM imaging result of a stent having a formulation of TH5 as indicated in Table 1. FIGS. 8 (*a*) and (*b*) show the SEM imaging result of a stent having a formulation of TH8 as indicated in Table 1. FIGS. 9 (*a*) and (*b*) show the SEM imaging result of a stent having a formulation of TH11 as indicated in Table 1. FIGS. 10 (*a*) and (*b*) show the SEM imaging result of a stent having a formulation of TH14 as indicated in Table 1. FIGS. 11 (*a*) and (*b*) show the SEM imaging result of a stent having a formulation of TH17 as indicated in Table 1. It can be seen from these results that these stents had very good morphology, and were nicely dispersed through the whole body of the stent. Consequently, they are very suitable for insertion and disposition into the human body, and should not cause significant or noticeable uncomfortable feeling to a patient one disposed inside the body of the patient.

Figure 12:
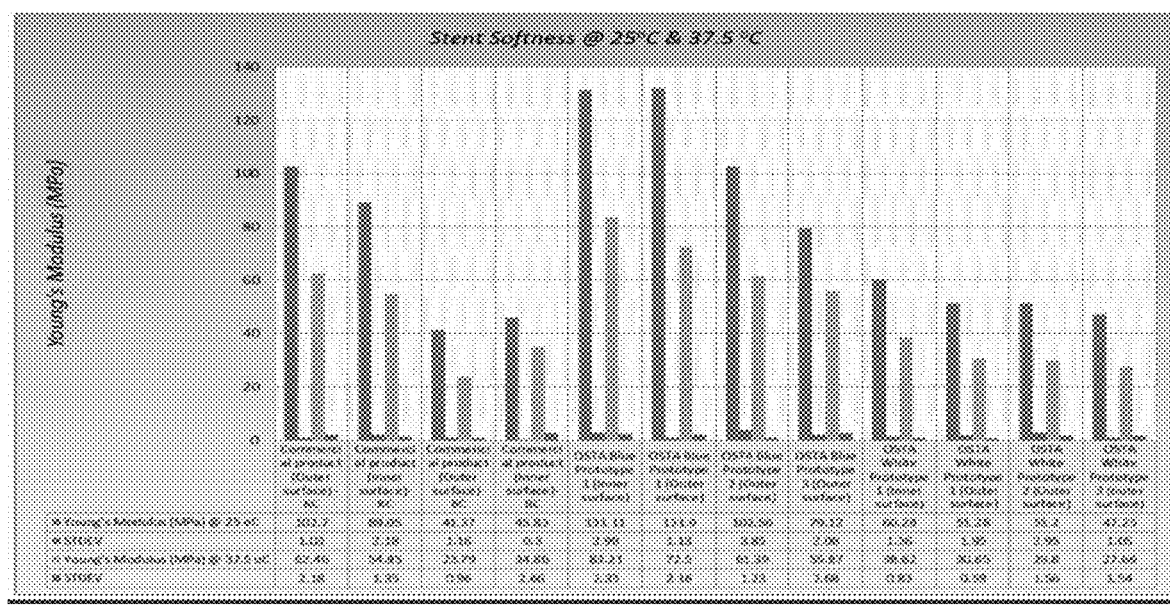
FIG. 12 shows a summary of softness measurement for several stents having different formulations.

FIG. 12 is an overall summary of stent softness for some of the representative stents. In particularly, OSTA Blue Prototype 1 corresponds to a stent having a formulation of TH2. OSTA Blue Prototype 2 corresponds to a stent having a formulation of TH5. OSTA Blue Prototype 3 corresponds to a stent having a formulation of TH8. OSTA White Prototype 1 corresponds to a stent having a formulation of TH11. OSTA White Prototype 2 corresponds to a stent having a formulation of TH 14. OSTA White Prototype 3 corresponds to a stent having a formulation of TH17. It can be seen from the results that these stents possessed very good softness properties, and are suitable for insertion and disposition into the body cavity of a patient.

INCORPORATION BY REFERENCE

The contents of all references, patents, pending patent applications and published patents, cited throughout this application are hereby expressly incorporated by reference.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed. It is intended that the following claims define the scope of the disclosure and that methods and structures within the scope of these claims and their equivalents be covered thereby.

What is claimed is:

1. A ureteral stent comprising ethylene-vinyl acetate in an amount of 9% to 30% by weight, and
   a mixture of barium sulfate, bismuth subcarbonate, bismuth oxychloride,
   a polyolefin elastomer, and a thermoplastics elastomer, in an amount of 45% to 90% by weight,
   wherein the ureteral stent has a transitional elastic modulus along an axial direction ranging from 0.5 cm to 40 cm of a total length of the ureteral stent being up to about 40 cm.

2. The ureteral stent of claim 1, wherein the stent comprises ethylene-vinyl acetate in an amount of 10% to 30% by weight.

3. The ureteral stent of claim 1, wherein the stent comprises ethylene-vinyl acetate in an amount of 15% to 25% by weight.

4. The ureteral stent of claim 1, wherein the stent comprises ethylene-vinyl acetate in an amount of 24% by weight.

5. The ureteral stent of claim 1, wherein the barium sulfate, bismuth subcarbonate, bismuth oxychloride, a polyolefin elastomer, and a thermoplastics elastomer, are in an amount of 45% to 85% by weight.

6. The ureteral stent of claim 1, wherein the barium sulfate, bismuth subcarbonate, bismuth oxychloride, a polyolefin elastomer, and a thermoplastics elastomer, are in an amount of 45% to 70% by weight.

7. The ureteral stent of claim 1, wherein the barium sulfate, bismuth subcarbonate, bismuth oxychloride, a polyolefin elastomer, and a thermoplastics elastomer, are in an amount of 45% by weight.

8. The ureteral stent of claim 1, wherein the stent has a density of between 0.933 to 0.952 g/cm$^3$.

9. The ureteral stent of claim 1, wherein the stent has a Vicat Softening temperature of 39 to 82° C.

10. The ureteral stent of claim 1, wherein the stent has a Vicat Softening temperature of 45° C.

11. The ureteral stent of claim 1, wherein the stent has a tensile stress of 11 to 26 MPa.

12. The ureteral stent of claim 1, wherein the stent has a tensile stress of 20 MPa.

13. The ureteral stent of claim 1, wherein the stent has an elastic modulus of 15 to 123 MPa.

14. The ureteral stent of claim 1, wherein the stent has an elastic modulus of 50 MPa.

15. A ureteral stent, comprising:
a body including an inner layer having a first elastic modulus value and an outer layer having a second elastic modulus value, the second elastic modulus value being greater than the first elastic modulus value,
wherein the body is formed from ethylene-vinyl acetate and:
a mixture of barium sulfate, bismuth subcarbonate, bismuth oxychloride,
a polyolefin elastomer and a thermoplastics elastomer, and
wherein the ethylene-vinyl acetate is in an amount of 9% to 30% by weight, and the mixture of a polyolefin elastomer and a thermoplastics elastomer are in an amount of 45% to 90% by weight
wherein the ureteral stent has a transitional elastic modulus along an axial direction ranging from 0.5 cm to 40 cm of a total length of the ureteral stent being up to about 40 cm.

16. The ureteral stent of claim 15, wherein the first elastic modulus value is 0.5 MPa to 50 MPa and the second elastic modulus value is 100 MPa to 200 Mpa.

* * * * *